United States Patent
Gerster et al.

(10) Patent No.: US 10,513,500 B2
(45) Date of Patent: Dec. 24, 2019

(54) CRYSTALLINE FORMS OF LESINURAD

(71) Applicant: Apotex Inc., Toronto (CA)

(72) Inventors: Jenny L. Gerster, Brantford (CA); Katherine A. Rantanen, Burlington (CA); Allan W. Rey, Brantford (CA)

(73) Assignee: Apotex Inc., Toronto (CA)

( * ) Notice: Subject to any disclaimer, the term of this patent is extended or adjusted under 35 U.S.C. 154(b) by 0 days.

(21) Appl. No.: 16/348,720

(22) PCT Filed: Nov. 9, 2017

(86) PCT No.: PCT/CA2017/051337
§ 371 (c)(1),
(2) Date: May 9, 2019

(87) PCT Pub. No.: WO2018/085932
PCT Pub. Date: May 17, 2018

(65) Prior Publication Data
US 2019/0263760 A1   Aug. 29, 2019

Related U.S. Application Data

(60) Provisional application No. 62/420,184, filed on Nov. 10, 2016.

(51) Int. Cl.
*C07D 249/12* (2006.01)
*C07D 213/82* (2006.01)

(52) U.S. Cl.
CPC ......... *C07D 249/12* (2013.01); *C07D 213/82* (2013.01); *C07B 2200/13* (2013.01)

(58) Field of Classification Search
CPC .. C07D 249/12; C07D 213/82; C07B 2200/13
See application file for complete search history.

(56) References Cited

U.S. PATENT DOCUMENTS

| | | | |
|---|---|---|---|
| 8,524,754 B2 | 9/2013 | Zamansky et al. | |
| 8,546,437 B2 | 10/2013 | Quart et al. | |
| 9,956,205 B2 | 5/2018 | Treiber et al. | |
| 9,969,701 B2 | 5/2018 | Chen et al. | |
| 2016/0297778 A1 | 10/2016 | Chen et al. | |

FOREIGN PATENT DOCUMENTS

| | | |
|---|---|---|
| CN | 104557748 A | 4/2015 |
| CN | 106831620 A | 6/2017 |
| CN | 106905250 A | 6/2017 |
| WO | 2009070740 A2 | 6/2009 |
| WO | 2011085009 A2 | 7/2011 |
| WO | 2012092395 A2 | 7/2012 |
| WO | 2015075561 A2 | 5/2015 |
| WO | 2015095703 A1 | 6/2015 |
| WO | 2017036884 A1 | 3/2017 |
| WO | 2018150335 A1 | 8/2018 |

OTHER PUBLICATIONS

Anonymous, "Process for the preparation of highly pure 2-((5-bromo-4-(cyclopropylnaphthalen-1-yl)-4H-1,2,4-triazol-3-yl)thio)acetic acid, salts thereof and solid state forms thereof," ip.com, Oct. 14, 2016.
Bernstein, "Polymorphism in Molecular Crystals," 2002, p. 9, Oxford University Press, New York.
"ICH Harmonised Tripartite Guideline—Impurities: Guideline for Residual Solvents Q3C(R5)," International Conference on Harmonisation of Technical Requirements for Registration of Pharmaceuticals for Human Use, Feb. 4, 2011.
Wang et al. "Discovery and Assessment of Atropisomers of (±)-Lesinurad," ACS Med. Chem. Lett., Feb. 14, 2017, 8, pp. 299-303, ACS Publications.

*Primary Examiner* — Timothy R Rozof
(74) *Attorney, Agent, or Firm* — The Webb Law Firm (57) ABSTRACT

The present invention provides novel crystalline forms of Lesinurad, pharmaceutical compositions including these crystalline forms, and their use in the treatment of hyperuricemia associated with gout. Specific crystalline forms provided by the present invention include Lesinurad Forms APO-I, a hemi-methanolate, APO-II, a hemi-ethanolate, and APO-III, a co-crystal of Lesinurad and nicotinamide.

15 Claims, 4 Drawing Sheets

CRYSTALLINE FORMS OF LESINURAD

CROSS-REFERENCE TO RELATED APPLICATIONS

This application is the United States national phase of International Application No. PCT/CA2017/051337 filed Nov. 9, 2017, and claims priority to U.S. Provisional Patent Application No. 62/420,184 filed Nov. 10, 2016, the disclosures of which are hereby incorporated by reference in their entirety.

TECHNICAL FIELD

The present invention is directed to novel crystalline forms of Lesinurad and processes for the preparation thereof.

BACKGROUND

The compound 2-((5-bromo-4-(4-cyclopropylnaphthalen-1-yl)-4H-1,2,4-triazol-3-yl)thio)acetic acid (1), commonly known as Lesinurad, is described in WO 2009/070740 A2, for instance, in Example 8. Lesinurad is marketed in the United States as ZURAMPIC®, and is indicated, in combination with a xanthine oxidase inhibitor, for the treatment of hyperuricemia associated with gout. Lesinurad is also marketed in the United States as DUZALLO®, a combination with the xanthine oxidase inhibitor Allopurinol, for the treatment of hyperuricemia associated with gout.

(1)

WO 2012/092395 A2 reports the preparation of two crystalline forms of Lesinurad, which are referred to as Form 1 and Form 2. According to the disclosure of WO 2012/092395, Form 1 can undergo conversion to Form 2 and is furthermore composed of a mixture of agglomerates of plate-like crystals. Form 2 is described as a free flowing solid having lower solubility than Form 1 in certain aqueous conditions. Further, the processes used to prepare these crystalline forms include steps that are not practical for use on a commercial scale.

WO 2015/075561 A2 describes crystalline Forms III, IV, V and VI of Lesinurad, as well as crystalline Forms α, β, γ, and δ of Lesinurad sodium salt. Form III is identified as being anhydrous, with hygroscopicity under some conditions. However, it is prepared from acetonitrile, which is an undesirable solvent to use for a final crystallization step. Form IV is identified as a dichloromethane solvate, Form V is identified as a 2-methyltetrahydrofuran solvate, and Form VI is identified as a trichloromethane solvate. However, according to the ICH (International Conference on Harmonisation) guidance document Q3C (R5): Impurities: Guideline for Residual Solvents, dichloromethane and trichloromethane are designated as Class 2 solvents, which limits the amounts of residual solvents that are permissible in a pharmaceutical product. Notably, when a 200 mg daily dose of Lesinurad is considered, the daily amounts of dichloromethane and trichloromethane that would be administered to a patient would exceed the limits allowed under the ICH guidelines. Thus, crystalline forms containing these solvents, such as Forms IV and VI, are impractical for commercial use. The Q3C guidance designates 2-methyltetrahydrofuran as a Class 4 solvent, which is a solvent that may also be of interest to manufacturers of excipients, drug substances, or drug products but for which no adequate toxicological data on which to base a permitted daily exposure (PDE) was found. In the case of Class 4 solvents, manufacturers are required to supply justification for residual levels of these solvents in pharmaceutical products. Thus, as for Forms IV and VI, Form V, the 2-methyltetrahydrofuran solvate, is not desirable for commercial use.

CN 104557748 A discloses crystalline Forms α and β. Form α, which is reported to contain between 13.1-17.3% (by weight GC) dichloromethane, is used as in intermediate in the formation of Form β. Accordingly, both forms suffer from the requirement that dichloromethane, a chlorinated Class 2 solvent in the ICH Guidance that is a potential carcinogen, be used in the manufacturing process. As discussed, for a 200 mg dose of Lesinurad, crystal forms containing large amounts of dichloromethane exceed the allowed daily exposure for the solvent.

WO 2015/095703 A1 relates to salts of Lesinurad and co-crystal forms of Lesinurad with proline and glycolic acid. Proline is an amino acid having a primary amine group with a pKa of approximately 10.6. As a result, proline is capable of forming either a salt or co-crystal with Lesinurad, which makes it a less favoured form owing to potential regulatory complications and implications associated with the characterization of the material. Glycolic acid, on the other hand, is a corrosive substance, which can be converted in the body to the toxic metabolite oxalic acid.

Different crystalline forms of the same compound may have different packing, thermodynamic, spectroscopic, kinetic, surface and mechanical properties. For example, different crystalline forms may have different stability properties. A particular crystalline form may be more sensitive to heat, relative humidity and/or light. Alternatively or additionally, a particular crystalline form may provide more compressibility and/or density properties thereby providing more desirable characteristics for formulation and/or product manufacturing. Particular crystalline forms may also have different dissolution rates, thereby providing different pharmacokinetic parameters, which allow for specific forms to be used in order to achieve specific pharmacokinetic targets. Differences in stability may result from changes in chemical reactivity, such as differential oxidation. Such properties may provide for more suitable product qualities, such as a dosage form that is more resistant to discolouration when comprised of a specific crystalline form. Different physical properties of crystalline forms may also affect their processing. For example, a particular crystalline form may be more resistant to flow, or may be more difficult to filter and/or wash.

Although general approaches to crystalline form screening of active pharmaceutical ingredients are known, it is well established that the prediction of whether any given compound will exhibit polymorphism is not possible. Furthermore, prediction of the properties of any unknown crystalline forms, and how they will differ from other crystalline forms of the same compound, remains even more elusive (Joel Bernstein, *Polymorphism in Molecular Crystals*, Oxford University Press, New York, 2002, page 9).

Known crystalline forms of Lesinurad are associated with various disadvantages, such as a propensity to convert to another crystalline form, particles that agglomerate, low solubility, hygroscopicity and incorporation of toxic or questionable solvents in manufacturing processes and co-crystal formers for which no adequate safety data is available. Therefore, there exists a need for novel crystalline forms of Lesinurad for use in providing improved drug products containing Lesinurad and their manufacture.

SUMMARY

The Lesinurad crystalline forms of the present invention exhibit differences in properties when compared to the known crystalline forms of Lesinurad. Additionally, the crystalline forms of the present invention can be prepared using more pharmaceutically acceptable solvents and co-crystal formers than known crystalline forms. For example, in aspects of the invention, ingredients are selected from the U.S. Food & Drug Administration's (FDA's) Generally Recognized As Safe (GRAS) list, which is an inventory of substances generally recognized as having been adequately shown to be safe under the conditions of intended use. Depending on the specific crystalline form of the invention used, properties that differ between the invention and the known crystalline forms of Lesinurad include the following: packing properties such as molar volume, density and hygroscopicity; thermodynamic properties such as melting point and solubility; kinetic properties such as dissolution rate and chemical/polymorphic stability; surface properties such as crystal habit; and mechanical properties such as hardness, tensile strength, compactibility, tableting, handling, flow, and blending. Furthermore, the crystalline forms of the present invention may be prepared by facile and industrially advantageous processes when compared to known crystalline forms of Lesinurad in the art.

Differences in the properties of the crystalline forms of the present invention provide practical advantages that can be exploited to meet specific needs in the manufacture and formulation of Lesinurad. For example, one or more crystalline forms of the present invention use solvents and reagents which are more pharmaceutically acceptable and environmentally friendly than the chlorinated solvents used to prepare some of the known forms of Lesinurad. Additionally, the crystalline forms of the present invention can, if desired, be prepared directly from a basic salt of Lesinurad, which is an upstream intermediate in known processes for the preparation of Lesinurad. As a result, the extra step of isolating a free form of Lesinurad is eliminated.

In a preferred embodiment, the present invention provides a co-crystal of Lesinurad and nicotinamide. Co-crystals provide the ability to alter the physicochemical properties of a drug substance while maintaining regulatory equivalency with an approved form of the same substance. According to the April 2013 FDA Guidance for Industry "Regulatory Classification of Pharmaceutical Co-Crystals", a co-crystal form, as opposed to a salt form, has a regulatory classification similar to that of a polymorph of the active pharmaceutical ingredient (API), and is therefore not regarded as a new API. As such, key properties of an API, such as solubility and stability, can be altered by the incorporation of one or more co-former molecules into the crystal lattice without requiring the submission of a new drug application (NDA) of an already approved form of the API. Instead, the co-crystal may be approved by an abbreviated new drug application (ANDA), which has fewer requirements, and is more facile. On the other hand, according to the current US regulatory scheme, different salt forms of the same active moiety, which may also allow for the alteration of physicochemical properties of an API, are considered different APIs.

Although co-crystals may be sought after, prediction of the properties of an as yet undiscovered co-crystal form of a substance is currently not possible. Further, there is no way to predict whether an API and co-former molecule will co-crystallize in the same crystal lattice, or the conditions under which co-crystallization will occur. Unlike the formation of salts, co-crystallization is not aided by the formation of a strong ionic bond between acidic and basic moieties, but instead relies upon weaker non-ionic interactions.

Advantageously, it has been found that the Lesinurad nicotinamide co-crystal of the present invention has improved properties compared to the previously described co-crystal of Lesinurad and proline. For example, the Lesinurad nicotinamide co-crystal of the present invention is chemically and physically stable in a humid and high temperature environment, whereas it has been found that the co-crystal of Lesinurad with proline that is disclosed in WO 2015/095703 A1 is hygroscopic in the same environment. Furthermore, unlike the Lesinurad proline co-crystal, which bears an amino group capable of undergoing proton exchange with the carboxylic acid of Lesinurad, the present invention provides a co-crystal of Lesinurad and nicotinamide, which is not capable of forming ionic bonds. The non-ionic nature of the intermolecular interactions between Lesinurad and nicotinamide in this co-crystal has been confirmed by single crystal X-ray diffraction (SCXRD) data.

Accordingly, in a first aspect of the present invention, there is provided a crystalline form of Lesinurad that is a $C_1$-$C_6$ alcohol solvate of Lesinurad. In a preferred embodiment of the first aspect, the solvate is a methanol or ethanol solvate of Lesinurad.

In a second aspect of the present invention, there is provided a crystalline form of Lesinurad characterized by a powder X-ray diffraction (PXRD) diffractogram comprising peaks, expressed in degrees 2θ (±0.2°), at 7.8°, 15.1° and 27.0°. In a preferred embodiment of the second aspect, the PXRD diffractogram further comprises at least three peaks, expressed in degrees 2θ (±0.2°), selected from the group consisting of: 14.5°, 15.6°, 16.4°, 17.6°, 18.5°, 19.9°, 22.1°, 23.5°, 25.9° and 29.3°. In a further preferred embodiment of the second aspect, the PXRD diffractogram further comprises peaks, expressed in degrees 2θ (±0.2°), at 14.5°, 15.6°, 16.4°, 17.6°, 18.5°, 19.9°, 22.1°, 23.5°, 25.9° and 29.3°. Preferably, the crystalline form of the second aspect has a weight percentage of methanol of at least approximately 3.0 wt %. More preferably, the crystalline form of the second aspect has a molar ratio of Lesinurad to methanol of approximately 1:0.5.

In a third aspect of the present invention, there is provided a crystalline form of Lesinurad characterized by a PXRD diffractogram comprising peaks, expressed in degrees 2θ (±0.2°), at 7.9°, 15.2°, 16.5° and 25.4°. In a preferred embodiment of the third aspect, the PXRD diffractogram further comprises at least two peaks, expressed in degrees 2θ (±0.2°), selected from the group consisting of: 14.4°, 15.7°, 17.7°, 18.4°, 22.1°, 22.8°, 23.5°, 26.5°, 28.8° and 29.3°. In a further preferred embodiment of the third aspect, the PXRD diffractogram further comprises peaks, expressed in degrees 2θ (±0.2°), at 14.4°, 15.7°, 17.7°, 18.4°, 22.0°, 22.8°, 23.5°, 26.5°, 28.8° and 29.3°. Preferably, the crystalline form of the third aspect has a weight percentage of ethanol of at least approximately 4.3 wt %. More preferably, the crystalline form of the third aspect has a molar ratio of Lesinurad to ethanol of approximately 1:0.5.

In a fourth aspect of the present invention, there is provided a co-crystal of Lesinurad with nicotinamide. Preferably, in the co-crystal of the fourth aspect, the molar ratio of Lesinurad to nicotinamide is approximately 1:1. In a preferred embodiment of the fourth aspect, the co-crystal is characterized by a PXRD diffractogram comprising peaks, expressed in degrees 2θ (±0.2°), at 6.2° and 19.9°. In a further preferred embodiment of the fourth aspect, the PXRD diffractogram further comprises at least four peaks, expressed in degrees 2θ (±0.2°), selected from the group consisting of: 7.6°, 10.3°, 14.1°, 15.3°, 17.8°, 21.1°, 23.4°, 25.7° and 27.2°. In another further preferred embodiment of the fourth aspect, the PXRD diffractrogram further comprises peaks, expressed in degrees 2θ (±0.2°), at 7.6°, 10.3°, 14.1°, 15.3°, 17.8°, 21.1°, 23.4°, 25.7° and 27.2°.

In a fifth aspect of the present invention, there is provided a pharmaceutical composition comprising a crystalline form of Lesinurad according to the first, second or third aspects of the invention, or the co-crystal of Lesinurad of the fourth aspect of the invention, and one or more pharmaceutically acceptable excipients. Preferably, the pharmaceutical composition is in the form of a solid dosage form. Most preferably, the pharmaceutical composition is a tablet. In a preferred embodiment of the fifth aspect, the composition comprises a crystalline form of Lesinurad according to the second aspect of the present invention. In another preferred embodiment of the fifth aspect, the composition comprises a crystalline form of Lesinurad according to the third aspect of the present invention. In another preferred embodiment of the fifth aspect, the composition comprises the Lesinurad co-crystal according to the fourth aspect of the present invention. Most preferably, the composition comprises the Lesinurad co-crystal according to the fourth aspect of the present invention. In a further preferred embodiment of the fifth aspect, the pharmaceutical composition further comprises a xanthine oxidase inhibitor, preferably Allopurinol.

In a sixth aspect of the present invention, there is provided a use of a crystalline form of Lesinurad according to the first, second or third aspects of the invention, or the co-crystal of Lesinurad of the fourth aspect of the invention, in the treatment of hyperuricemia. Preferably, the hyperuricemia treated is hyperuricemia associated with gout. In a preferred embodiment of the sixth aspect, the crystalline form of Lesinurad according to the second aspect of the invention is used. In another preferred embodiment of the sixth aspect, the crystalline form of Lesinurad according to the third aspect of the invention is used. In another preferred embodiment of the sixth aspect, the co-crystal of Lesinurad of the fourth aspect of the invention is used. Most preferably, the co-crystal of Lesinurad of the fourth aspect of the invention is used. In a further preferred embodiment of the sixth aspect, the treatment of hyperuricemia associated with gout is in combination with a xanthine oxidase inhibitor. Preferably, the xanthine oxidase inhibitor is Allopurinol.

Other aspects and features of the present invention will become apparent to those ordinarily skilled in the art upon review of the following description of specific embodiments of the invention in conjunction with the accompanying figures.

BRIEF DESCRIPTION OF THE DRAWINGS

Embodiments of the present invention are described, by way of example only, with reference to the attached Figures.

DETAILED DESCRIPTION

The present invention provides novel crystalline forms of Lesinurad providing improved properties when compared to the known crystalline forms of Lesinurad. Further, the novel crystalline forms of the present invention can be prepared using more pharmaceutically acceptable solvents and co-crystal formers than known crystalline forms of Lesinurad. Depending on the specific crystalline form of the invention used, properties that differ between the invention and the known crystalline forms of Lesinurad include the following: packing properties such as molar volume, density and hygroscopicity; thermodynamic properties such as melting point and solubility; kinetic properties such as dissolution rate and chemical/polymorphic stability; surface properties such as crystal habit; and mechanical properties such as hardness, tensile strength, compactibility, tableting, handling, flow, and blending. Furthermore, the crystalline forms of the present invention may be prepared by facile and industrially advantageous processes when compared to the crystalline forms of Lesinurad known in the art. The improved properties provided by the novel crystalline forms of the present invention provide practical advantages over known forms of Lesinurad that can be exploited to meet specific needs in the manufacture and formulation of Lesinurad.

Depending on the nature of the methodology applied and the scale selected to display results obtained from an X-ray diffraction analysis, the intensity of a peak obtained may vary quite dramatically. For example, it is possible to obtain a relative peak intensity of 1% when analyzing one sample of a substance, but another sample of the same substance may show a much different relative intensity for a peak at the same position. This may be due, in part, to the preferred orientation of the sample and its deviation from the ideal random sample orientation, sample preparation and the methodology applied. Such variations are known and understood by a person of skill in the art.

As used herein, the term 'crystalline form' or 'form' refers to a substance with a particular arrangement of molecular components in its crystal lattice, and which may be identified by physical characterization methods such as PXRD. As used herein, the term crystalline form is intended to include single-component and multiple-component crystalline forms of Lesinurad. Single-component forms of Lesinurad consist solely of Lesinurad in the crystal lattice. Multiple-component forms of Lesinurad include solvates, hydrates and co-crystals of Lesinurad wherein a solvent, water or co-crystal former is also incorporated into the crystal lattice. In both single-component and multiple-component forms, there can exist more than one three-dimensional arrangement of components in the crystal lattice, which may give rise to differences in physical properties and which can be detected by physical characterization methods, such as PXRD. Where the exact nature of a multiple-component system is not explicitly stated, the form shall be identified by the physical characterization data such as PXRD.

Multi-component crystalline forms comprising more than one type of molecule, such as co-crystals and solvates (including hydrates), may have some variability in the exact molar ratio of their components depending on a variety of conditions used. For example, a molar ratio of components within a solvate or co-crystal provides a person of skill in the art information as to the general relative quantities of the components of the solvate or co-crystal. In many cases, the molar ratio may vary by ±20% from a stated range. For example, with respect to the present invention, a molar ratio of 1:0.5 should be understood to include the ratios 1:0.4 and 1:0.6, as well as all of the individual ratios in between.

As used herein, when referring to a solvent content, the term "weight percentage" (wt %) refers to the ratio: weight solvent/(weight solvent+weight Lesinurad), expressed as a percentage.

As used herein, the term "room temperature" refers to a temperature in the range of 20° C. to 25° C.

Unless defined otherwise herein, the term "approximately", when used in reference to a weight percentage, allows for a variance of plus or minus 10%.

When describing the embodiments of the present invention there may be a common variance to a given temperature or time that would be understood or expected by the person skilled in the art to provide substantially the same result. For example, when reference is made to a particular temperature, it is to be understood by the person skilled in the art that there is an allowable variance of ±5° C. associated with that temperature. When reference is made to a particular time, it is to be understood that there is an allowable variance of ±10 minutes when the time is one or two hours, and ±1 hour when longer periods of time are referenced.

In a first embodiment of the present invention, there is provided a crystalline form of Lesinurad that is a $C_1$-$C_6$ alcohol solvate of Lesinurad. Preferably the solvate is a methanol or ethanol solvate of Lesinurad.

In a second embodiment of the present invention, there is provided a new crystalline form of Lesinurad, Lesinurad Form APO-I, having a weight percentage methanol of at least approximately 3.0 wt %, and preferably approximately 3.8 wt %. Preferably, the molar ratio of Lesinurad to methanol is approximately 1:0.5, corresponding to a hemi-methanol solvate.

Lesinurad Form APO-I can be characterized by a PXRD diffractogram comprising, among other peaks, characteristic peaks, expressed in degrees 2θ (±0.2°), at 7.8°, 15.1° and 27.0°. Preferably, the PXRD diffractogram further comprises at least three peaks, expressed in degrees 2θ (±0.2°), selected from the group consisting of: 14.5°, 15.6°, 16.4°, 17.6°, 18.5°, 19.9°, 22.1°, 23.5°, 25.9° and 29.3°. More preferably, the PXRD diffractogram further comprises peaks, expressed in degrees 2θ (±0.2°), at 14.5°, 15.6°, 16.4°, 17.6°, 18.5°, 19.9°, 22.1°, 23.5°, 25.9° and 29.3°. PXRD studies of a capped sample of Lesinurad Form APO-I have shown that this crystal form is stable following storage in a stability chamber maintained at 27° C./60% RH for 17 days.

Figure 1:
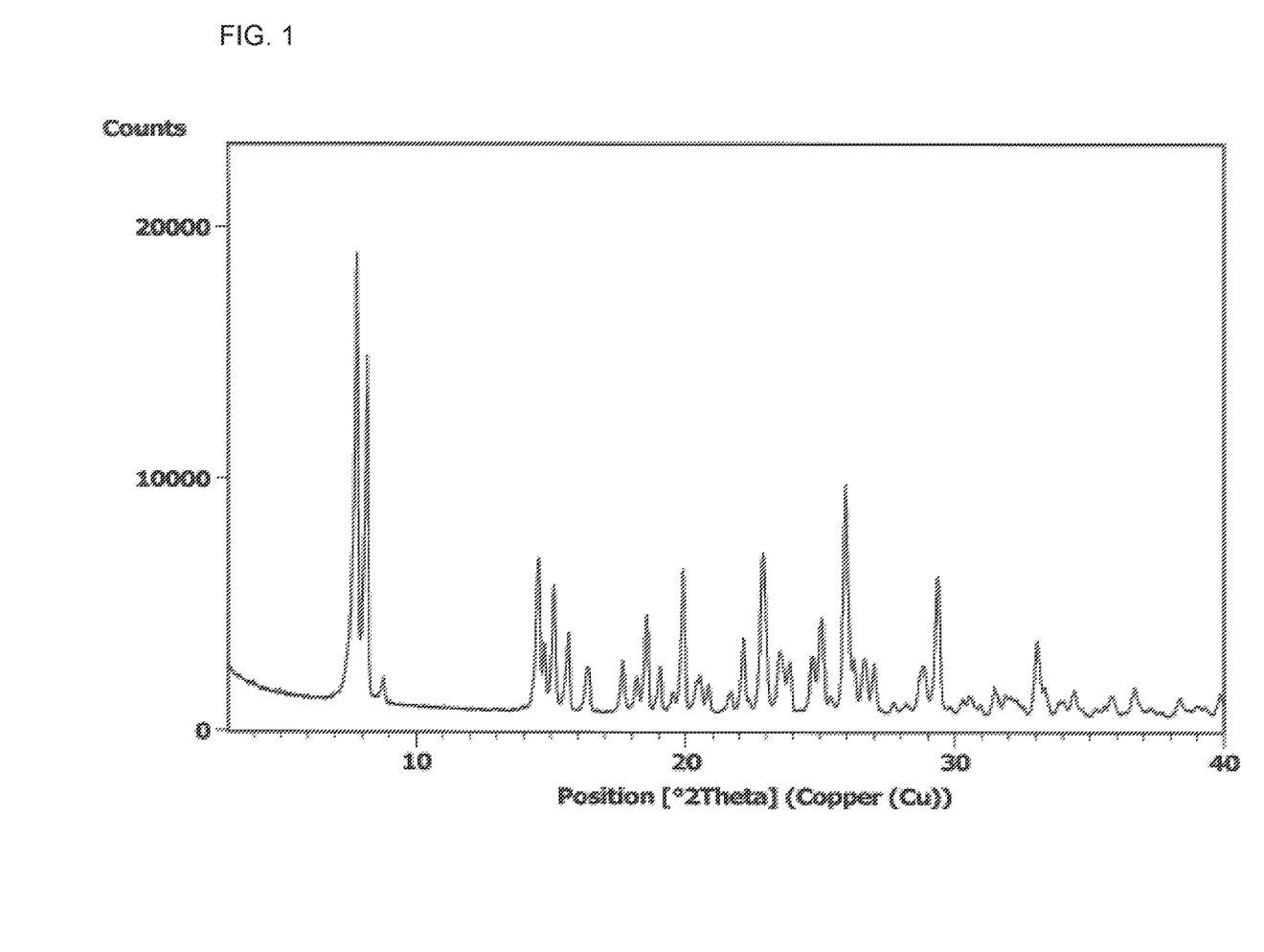
FIG. 1 is a PXRD diffractogram of Lesinurad Form APO-I.

An illustrative PXRD diffractogram of Lesinurad Form APO-I is shown in FIG. 1. A peak listing, comprising peaks from the PXRD diffractogram in FIG. 1, and their relative intensities, is provided in Table 1. Although illustrative of the PXRD diffractogram that is provided for the Lesinurad Form APO-I of the present invention, the relative intensities of the peaks are variable. Thus, depending on a particular sample, the prominence or relative intensity of the peaks observed may differ from those in the illustrative PXRD diffractogram and peak listing.

TABLE 1

Relative peak intensities of
Lesinurad Form APO-I from FIG. 1

| Angle (° 2θ) | Relative intensity (%) |
|---|---|
| 7.77 | 100.00 |
| 8.15 | 75.91 |
| 8.77 | 5.71 |
| 14.52 | 33.13 |
| 14.75 | 12.60 |
| 15.10 | 28.40 |
| 15.62 | 18.98 |
| 16.36 | 11.51 |
| 17.64 | 11.47 |
| 18.17 | 7.05 |
| 18.53 | 22.11 |
| 19.03 | 10.29 |
| 19.52 | 3.72 |
| 19.90 | 33.45 |
| 20.41 | 6.09 |
| 20.83 | 6.22 |
| 21.62 | 4.02 |
| 22.12 | 17.45 |
| 22.87 | 35.43 |
| 23.52 | 12.37 |
| 23.84 | 11.14 |
| 24.66 | 8.98 |
| 25.08 | 16.53 |
| 25.93 | 49.47 |
| 26.63 | 10.01 |
| 26.98 | 10.22 |
| 28.80 | 7.35 |
| 29.33 | 32.14 |

As described in Example 3, Lesinurad Form APO-I can be prepared from a solution of Lesinurad in methanol through the drop-wise addition of an equivalent amount of water. Filtration of the resulting suspension provides Lesinurad Form APO-I having a PXRD diffractogram consistent with that of FIG. 1.

Alternatively, Lesinurad Form APO-I can be prepared by, among other methods, the method described in Example 1, where Lesinurad is dissolved in methanol with heating to approximately 50° C., following by a cooling period during which crystallization occurs. Following filtration, Lesinurad Form APO-I is obtained. Optionally, hot filtration can be performed to ensure complete dissolution of the Lesinurad used as a starting material.

A further alternative preparation of Lesinurad Form APO-I is described in Example 6 wherein Lesinurad Form APO-I is prepared from Lesinurad sodium salt. Lesinurad sodium salt is dissolved in methanol, with sonication to facilitate complete dissolution, if needed. To this solution is added a solution containing an equimolar amount of hydrogen chloride in isopropanol or other suitable solvent. The resulting precipitate can be filtered to obtain Lesinurad Form APO-I.

In a third embodiment of the present invention, there is provided a second new crystalline form of Lesinurad, Lesinurad Form APO-II, having a weight percentage ethanol of at least approximately 4.3 wt %, and preferably approximately 5.4 wt %. In a preferred embodiment of Lesinurad Form APO-II, the molar ratio of Lesinurad to ethanol is approximately 1:0.5, corresponding with a hemi-ethanol solvate.

Lesinurad Form APO-II can be characterized by a PXRD diffractogram comprising, among other peaks, characteristic peaks, expressed in degrees 2θ (±0.2°), at 7.9°, 15.2°, 16.5° and 25.4°. Preferably, the PXRD diffractogram further comprises at least two peaks, expressed in degrees 2θ (±0.2°), selected from the group consisting of: 14.4°, 15.7°, 17.7°, 18.4°, 22.1°, 22.8°, 23.5°, 26.5°, 28.8° and 29.3°. More preferably, the PXRD diffractogram further comprises peaks, expressed in degrees 2θ (±0.2°), at 14.4°, 15.7°, 17.7°, 18.4°, 22.1°, 22.8°, 23.5°, 26.5°, 28.8° and 29.3°. PXRD studies of a capped sample of Lesinurad Form APO-II have shown that this crystal form is stable following storage at room temperature and ambient humidity for 28 days.

Figure 2:
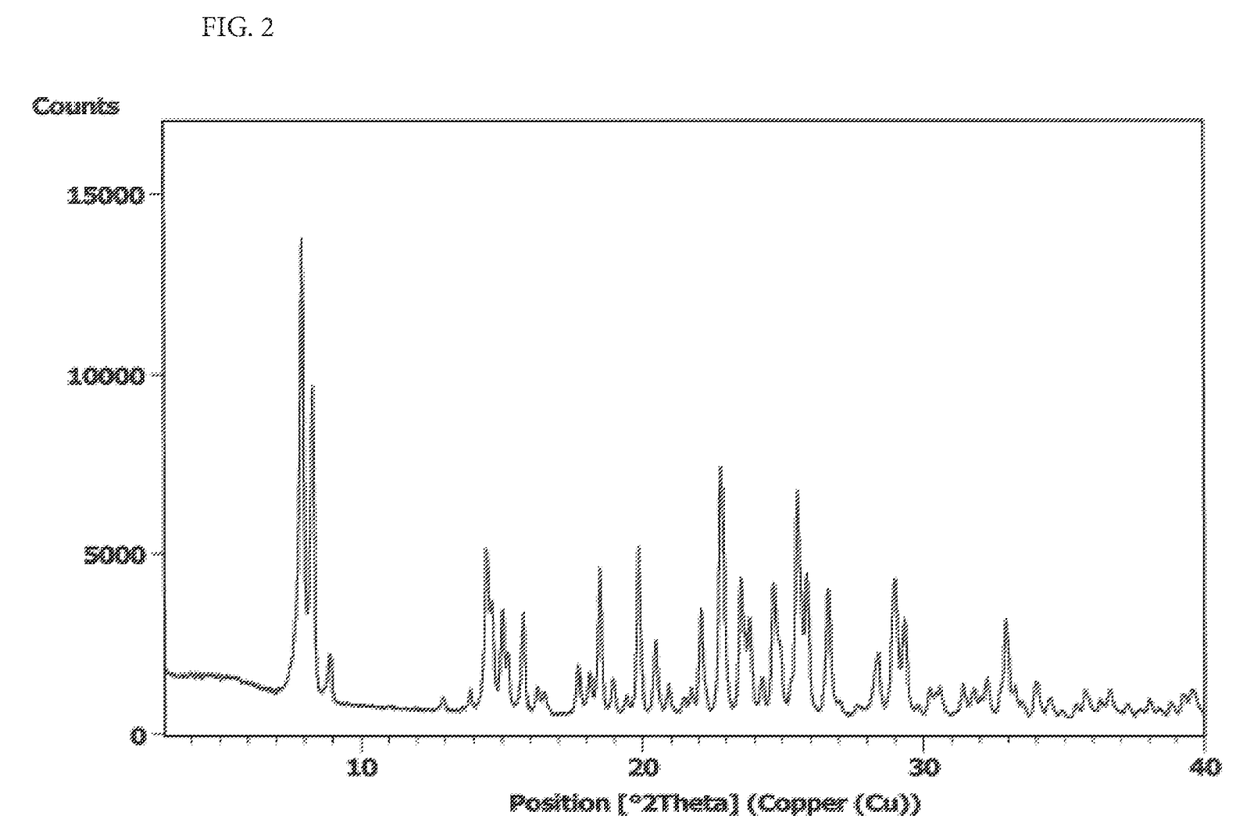
FIG. 2 is a PXRD diffractogram of Lesinurad Form APO-II.

An illustrative PXRD diffractogram of Lesinurad Form APO-II is shown in FIG. 2. A peak listing, comprising peaks from the PXRD diffractogram in FIG. 2, and their relative intensities, is provided in Table 2. Although illustrative of the PXRD diffractogram that is provided for the Lesinurad Form APO-II of the present invention, the relative intensities of the peaks are variable. Thus, depending on a particular sample, the prominence or relative intensity of the peaks observed may differ from those in the illustrative PXRD diffractogram and peak listing.

TABLE 2

Relative peak intensities of Lesinurad Form APO-II from FIG. 2

| Angle (° 2θ) | Relative intensity (%) |
| --- | --- |
| 7.88 | 40.38 |
| 8.24 | 100.00 |
| 8.88 | 5.48 |
| 12.82 | 1.06 |
| 13.79 | 1.86 |
| 14.39 | 11.91 |
| 14.59 | 11.14 |
| 14.97 | 7.51 |
| 15.19 | 10.39 |
| 15.72 | 9.13 |
| 16.22 | 2.20 |
| 16.45 | 4.91 |
| 17.74 | 4.71 |
| 18.04 | 4.14 |
| 18.42 | 13.95 |
| 18.94 | 3.17 |
| 19.39 | 1.71 |
| 19.82 | 14.18 |
| 20.40 | 9.91 |
| 20.85 | 4.94 |
| 22.05 | 8.51 |
| 22.80 | 31.46 |
| 23.52 | 17.76 |
| 24.56 | 9.29 |
| 25.44 | 15.14 |
| 25.79 | 7.54 |
| 26.54 | 10.20 |
| 28.80 | 13.91 |
| 29.31 | 6.90 |

As described in Example 8, Lesinurad Form APO-II can be prepared from a solution of Lesinurad in anhydrous ethanol by heating the solution to approximately 50° C., conducting hot filtration, if necessary, to ensure the complete dissolution of Lesinurad, and allowing the solution to cool, during which time crystallization occurs. Filtration of the resulting material provides Lesinurad Form APO-II having a PXRD diffractogram consistent with that of FIG. 2.

Alternatively, Lesinurad Form APO-II can be prepared by, among other methods, the method described in Example 9, where Lesinurad is dissolved in ethanol followed by the dropwise addition of water. Following filtration of the resulting precipitate, Lesinurad Form APO-II is obtained.

A further alternative preparation of Lesinurad Form APO-II is described in Example 11 wherein Lesinurad Form APO-II is prepared from Lesinurad sodium salt. Lesinurad sodium salt is dissolved in ethanol, with sonication to facilitate complete dissolution, if needed. To this solution is added a solution containing an approximately equimolar amount of hydrogen chloride in isopropanol or other suitable solvent. The resulting precipitate can be filtered to obtain Lesinurad Form APO-II.

In a fourth embodiment of the present invention, there is provided a third new crystalline form of Lesinurad, a co-crystal of Lesinurad with nicotinamide, Lesinurad Form APO-III, wherein the molar ratio of Lesinurad to nicotinamide is approximately 1:1.

Lesinurad Form APO-III can be characterized by a PXRD diffractogram comprising, among other peaks, characteristic peaks, expressed in degrees 2θ (±0.2°), at 6.2° and 19.9°. Preferably, the PXRD diffractogram further comprises at least four peaks, expressed in degrees 2θ (±0.2°), selected from the group consisting of: 7.6, 10.3°, 14.1°, 15.3°, 17.8°, 21.1°, 23.4°, 25.7° and 27.2°. More preferably, the PXRD diffractogram further comprises peaks, expressed in degrees 2θ (±0.2°), at 7.6°, 10.3°, 14.1°, 15.3°, 17.8°, 21.1°, 23.4°, 25.7° and 27.2°. PXRD studies of capped and uncapped samples of Lesinurad Form APO-III have shown that this crystal form is stable following storage in stability chambers maintained at 27° C./60% RH and 40° C./75% RH for 18 days.

Figure 3:
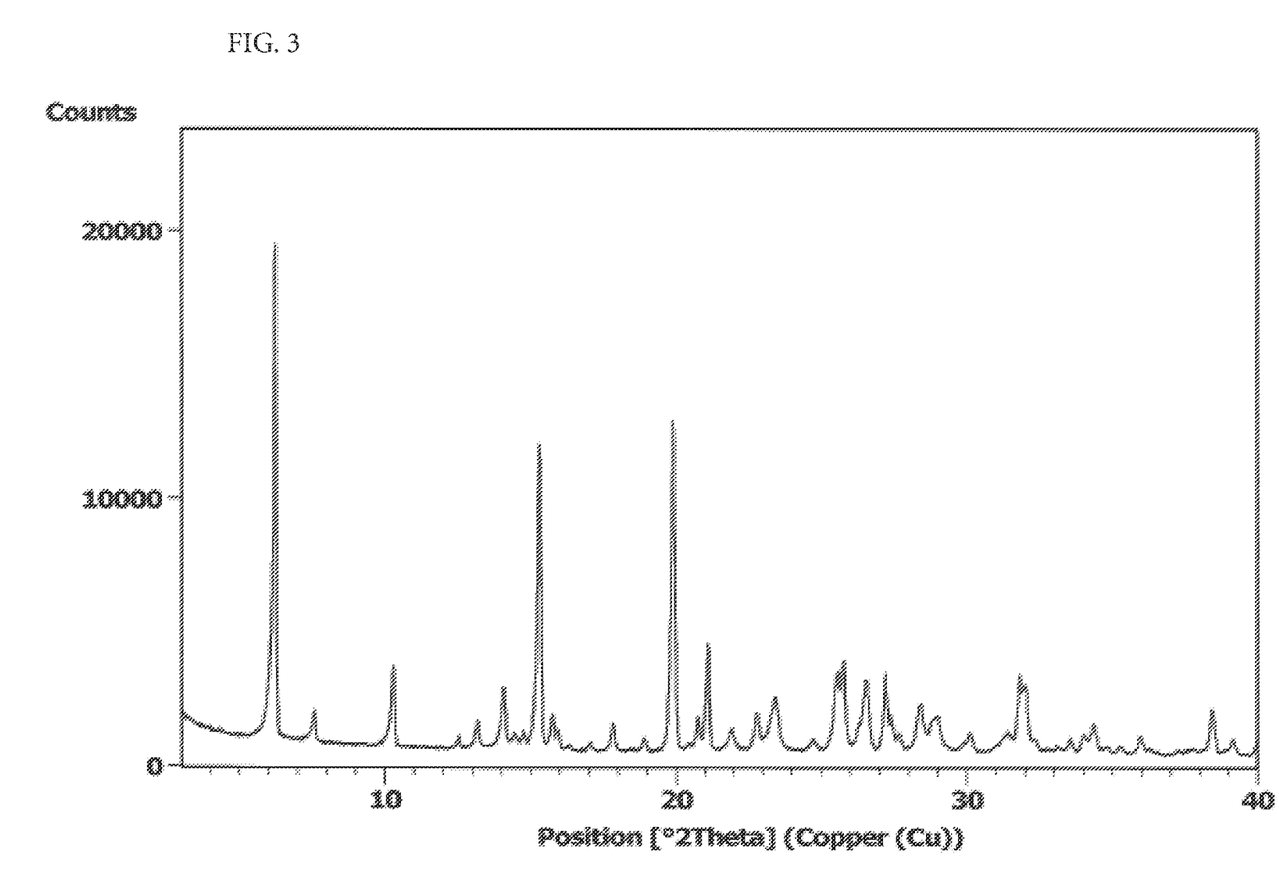
FIG. 3 is a PXRD diffractogram of Lesinurad Form APO-III.

An illustrative PXRD diffractogram of Lesinurad Form APO-III is shown in FIG. 3. A peak listing, comprising peaks from the PXRD diffractogram in FIG. 3, and their relative intensities, is provided in Table 3. Although illustrative of the PXRD diffractogram that is provided for the Lesinurad Form APO-III of the present invention, the relative intensities of the peaks are variable. Thus, depending on a particular sample, the prominence or relative intensity of the peaks observed may differ from those in the illustrative PXRD diffractogram and peak listing.

TABLE 3

Relative peak intensities of Lesinurad Form APO-III from FIG. 3

| Angle (° 2θ) | Relative intensity (%) |
| --- | --- |
| 6.20 | 100.00 |
| 7.55 | 6.84 |
| 10.26 | 18.30 |
| 13.16 | 5.79 |
| 14.05 | 12.57 |
| 14.44 | 2.61 |
| 14.75 | 2.58 |
| 15.28 | 63.71 |
| 15.74 | 6.80 |
| 15.93 | 4.10 |
| 17.82 | 6.29 |
| 19.89 | 70.92 |
| 20.75 | 6.55 |
| 21.07 | 22.84 |
| 21.88 | 4.32 |
| 22.76 | 7.64 |
| 23.38 | 9.42 |
| 25.47 | 10.86 |
| 25.74 | 18.82 |
| 26.52 | 14.22 |
| 27.18 | 16.53 |
| 28.36 | 8.28 |
| 28.97 | 5.58 |

As described in Example 12, Lesinurad Form APO-III can be prepared by heating a suspension of approximately equimolar amounts of Lesinurad and nicotinamide in ethanol to about 75° C. Following slow cooling, Lesinurad Form APO-III is isolated by filtration to provide a material having a PXRD diffractogram consistent with that of FIG. 3.

Optionally, if available, seed crystals of Lesinurad Form APO-III can be added during the crystallization process to facilitate crystallization.

Figure 4:
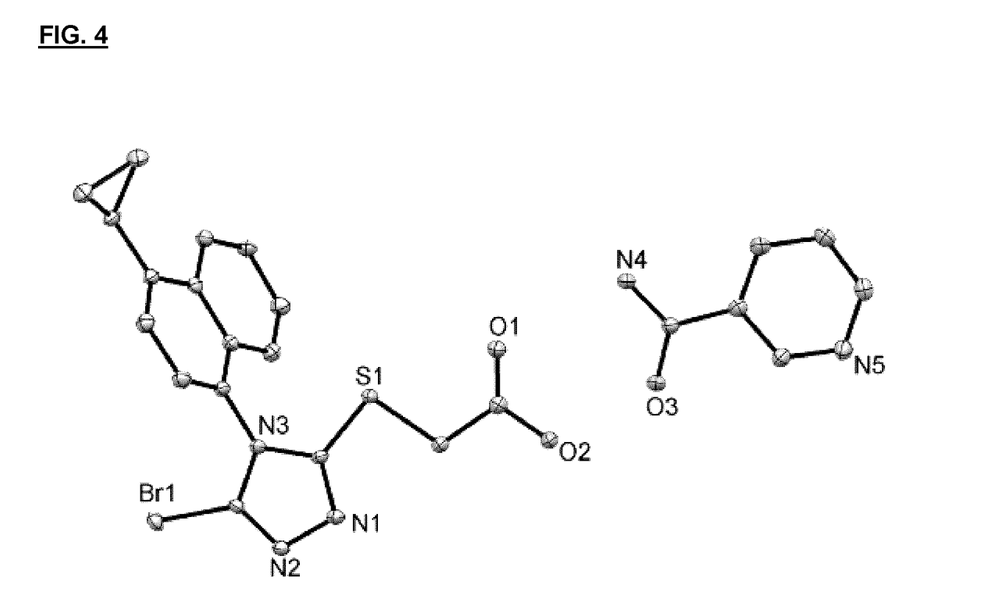
FIG. 4 is an Oak Ridge Thermal Ellipsoid Plot (ORTEP) illustration of the SCXRD of Form APO-III.

Single crystals of Lesinurad Form APO-III were grown from a layered solution of Lesinurad and nicotinamide (following dissolution of Form APO-III) in DMSO and acetone as described in Example 15, and characterized by SCXRD. A summary of the SCXRD data is provided in Table 4, and an ORTEP illustration of the molecular structure is shown in FIG. 4. This illustration confirms that Form APO-III is a 1:1 Lesinurad:nicotinamide co-crystal, i.e., the molar ratio of Lesinurad to nicotinamide is 1:1.

TABLE 4

Single Crystal X-Ray Diffraction Parameters of the 1:1 Lesinurad:nicotinamide co-crystal (Form APO-III)

| | |
|---|---|
| Formula | $C_{23}H_{20}BrN_5O_3S$ |
| Formula Weight (g/mol) | 526.41 |
| Crystal System | monoclinic |
| Space Group | $P2_1/c$ |
| Temperature, K | 110 |
| a, Å | 14.069 (4) |
| b, Å | 6.7904 (16) |
| c, Å | 23.064 (7) |
| α, ° | 90 |
| β, ° | 95.349 (11) |
| γ, ° | 90 |
| V, Å$^3$ | 2193.9 (11) |
| Z | 4 |
| ρ (g/cm) | 1.594 |
| λ, Å, (CuKα) | 0.71073 |
| Measured fraction of data | 0.997 |
| Unique reflections measured/ reflections included in refinement | 8761 |
| $R_1$ | 0.0537 |
| $wR_2$ | 0.1228 |
| $R_1$ (all data) | 0.0804 |
| $wR_2$ (all data) | 0.1340 |
| Goodness of Fit | 1.046 |
| Min & Max peak heights on final ΔF Map (e$^-$/Å) | −0.841, 2.987 |

In a further embodiment of the invention, there is provided a pharmaceutical composition comprising a crystalline form of Lesinurad or a co-crystal of Lesinurad with one or more pharmaceutically acceptable excipients. Preferably, the pharmaceutical composition is a solid dosage form suitable for oral administration, such as a capsule, tablet, pill, powder or granules. Most preferably, the pharmaceutical composition is a tablet. Preferably, the pharmaceutical composition provides a dose of Lesinurad that is equivalent to the 200 mg of Lesinurad found in ZURAMPIC® tablets.

Suitable pharmaceutically acceptable excipients are preferably inert with respect to the crystalline form or co-crystal of Lesinurad, and may include, for example, one or more excipients selected from binders such as starches, diluents or fillers such as lactose, lubricants such as talc or magnesium stearate, surface active agents, and dispersing agents. The preparation of solid oral dosage forms is well known to a person of skill in the art, and is described generally, for example, in *Remington The Science and Practice of Pharmacy* 21$^{st}$ *Edition* (Lippincott Williams & Wilkins: Philadelphia; 2006; Chapter 45).

Optionally, the solid dosage forms may be prepared with coatings and shells, such as enteric coatings and extended release coatings, using standard pharmaceutical coatings. Such coatings, and their application, are well known to persons skilled in the art, and are described, for example, in *Remington The Science and Practice of Pharmacy* 21$^{st}$ *Edition* (Lippincott Williams & Wilkins: Philadelphia; 2006; Chapter 47).

Optionally, pharmaceutical compositions according to the present invention can be prepared with other medicinal ingredients for use in combination therapy. Alternatively, combination therapy using the Lesinurad crystalline form or co-crystal of the present invention can involve individual pharmaceutical compositions for each medicinal ingredient, which are administered concurrently or sequentially.

Preferably, when used in combination therapy, the crystalline form or co-crystal of Lesinurad of the present invention is used in combination with a xanthine oxidase inhibitor. Most preferably, the xanthine oxidase inhibitor is Allopurinol. Thus, in one embodiment of the present invention, there is provided a pharmaceutical composition comprising a fixed dose combination of a crystalline form or co-crystal of Lesinurad according to the present invention with a xanthine oxidase inhibitor, preferably Allopurinol. Pharmaceutical compositions containing a combination of active ingredients may be prepared in the same manner as described above. Preferably, in such fixed dose combinations, the pharmaceutical composition provides doses of Lesinurad and Allopurinol that are equivalent to those found in DUZALLO® tablets. Thus, preferred fixed dose combination tablets will comprise the equivalent of 200 mg Lesinurad and 200 mg or 300 mg of Allopurinol.

EXAMPLES

The following non-limiting examples are illustrative of some of the aspects and embodiments of the invention described herein.

The Lesinurad used as a starting material in the following examples was consistent with that of Lesinurad Form 2, which is reported in WO 2012/092395 A2. Other polymorphic forms may be equally suitable as starting material when preparing the novel crystalline forms of Lesinurad of the present invention.

Powder X-Ray Diffraction Analysis:

Data were acquired on a PANanalytical X-Pert Pro MPD diffractometer with fixed divergence slits and an X'Celerator RTMS detector. The diffractometer was configured in Bragg-Brentano geometry; data was collected over a 2-theta range of 3° to 40° using CuKα radiation at a power of 40 mA and 45 kV. Cup radiation was removed using a divergent beam nickel filter. A step size of 0.017° was used. Samples were rotated to reduce preferred orientation effects. Samples were lightly ground prior to analysis.

Single Crystal Data Collection and Processing

Samples for SCXRD analysis were mounted on a MiTe-Gen polyimide micromount with a small amount of PARATONE® N oil. All X-ray measurements were made on a Bruker Kappa Axis Apex2 diffractometer at a temperature of 110 K. The unit cell dimensions were determined from a symmetry constrained fit of 9936 reflections with 4.8°<2θ<60.84°. The data collection strategy was a number of ω and φ scans which collected data up to 67.586° (2θ). Frame integration was performed using SAINT (Bruker-AXS, SAINT Version 2013.8, 2013). The resulting raw data was scaled and absorption corrected using a multi-scan averaging of symmetry equivalent data using SADABS (Bruker-AXS, SADABS Version 2012.1, 2012).

Single Crystal Structure Solution and Refinement

Single crystal structures were solved by using a dual space methodology with the SHELXT program (Sheldrick, G. M., *Acta Cryst.* 2015, A71, 3-8). Most non-hydrogen atoms were obtained from the initial solution. The remaining atoms and the distinct atom positions from the disorder were obtained from subsequent difference Fourier maps. The hydrogen atoms were introduced at idealized positions and were allowed to ride on the parent atom. The normalized occupancy of the major disorder component refined to a value of 0.95222(7). The disorder can be described as a pivot primarily about the N3-C5 bond. The structural model was fit to the data using full matrix least-squares based on $F^2$. Calculated structure factors include corrections for anomalous dispersion from the usual tabulation. Structure refinement was conducted using the SHELXL-2014 program from the SHELX suite of crystallographic software (Sheldrick, G. M., *Acta Cryst.* 2015, C71, 3-8). Graphic plots were produced using the NRCVAX program suite (Gabe, E. J.; Le Page, Y.; Charland, J. P.; Lee, F. L. and White, P. S. *J. Appl. Cryst.* 1989, 22, 384-387).

Example 1: Preparation of Lesinurad Form APO-I

Lesinurad (200 mg, 0.495 mmol) was weighed into a vial and suspended in HPLC grade methanol (1 mL). The suspension was immersed in a reactor block pre-heated to 50° C. After stirring for 20 minutes, a further portion (0.4 mL) of methanol was added and the mixture stirred for 10 minutes. Hot filtration was performed and precipitation started to occur instantly. Following stirring for three hours, filtration of the precipitate afforded Lesinurad Form APO-I. The PXRD diffractogram of a sample prepared by this method is shown in FIG. 1.

Example 2: Preparation of Lesinurad Form APO-I

A solution of Lesinurad (200 mg, 0.495 mmol) in methanol (5 mL) was filtered for clarification before distilled water was added drop wise until cloudiness persisted (5 mL). Following stirring for about 18 hours at room temperature, filtration of the precipitate afforded Lesinurad Form APO-I (215 mg). The PXRD diffractogram of the sample after brief aspirator drying was consistent with FIG. 1. Drying in vacuo at room temperature for 3 hours afforded Lesinurad having a weight percentage methanol of 5.3 wt % by $^1$H-NMR. Further drying of the sample at room temperature for about 3 days afforded Lesinurad having a weight percentage methanol of 3.5 wt %.

Example 3: Preparation of Lesinurad Form APO-I

A solution of Lesinurad (1.5 g, 3.7 mmol) in HPLC grade methanol (37.5 mL) was obtained by stirring and sonication. The solution was clarified by gravity filtration before drop wise addition of distilled water (38 mL) via addition funnel. A turbid solution was observed upon addition of approximately 18 mL of the water and addition of the remaining 20 mL produced a milky suspension that was stirred for about 4 hours at room temperature. The precipitate was collected by filtration and dried by aspiration for several minutes, affording Lesinurad Form APO-I (1.8 g). The PXRD diffractogram of the solid was consistent with FIG. 1.

Example 4: Preparation of Lesinurad Form APO-I

A mixture of Lesinurad sodium salt (250 mg, 0.587 mmol) in HPLC grade methanol (1.3 mL) was sonicated to achieve dissolution. To this solution was added a hydrogen chloride solution (20 wt % in isopropanol, 107 mg, 0.587 mmol), resulting in immediate formation of a white suspension that was stirred at room temperature for about 3.5 hours. Filtration of the mixture afforded a white solid (168 mg, 66% yield) having a PXRD consistent with FIG. 1.

Example 5: Preparation of Lesinurad Form APO-I

A suspension of Lesinurad (200 mg, 0.495 mmol) in HPLC grade methanol (1.4 mL) was dissolved in a reactor block pre-heated to 50° C. Upon hot filtration, rapid precipitation began and the resulting mixture was stirred for 3 hours. The solid was collected by filtration to afford Lesinurad Form APO-I (94.1 mg, 44% yield) having a PXRD diffractogram consistent with FIG. 1.

Example 6: Preparation of Lesinurad Form APO-I

A mixture of Lesinurad sodium salt (2.0 g, 4.7 mmol) in HPLC grade methanol (11 mL) was sonicated to achieve dissolution (5 minutes). To this solution was added a hydrogen chloride solution (20 wt % in isopropanol, 0.86 g, 4.7 mmol) drop wise over 5 minutes. Immediate formation of a milky white precipitate was observed, and the mixture stirred for about 3.5 hours before gradual concentration under a steady nitrogen stream for 0.5 hour. The precipitated material was collected by filtration and dried under aspiration for 5 minutes, affording Lesinurad Form APO-I (0.72 g, 35% yield) as a colourless solid. The material was further dried at room temperature in vacuo for 3.5 hours. PXRD analysis before and after drying was consistent with FIG. 1. TGA analysis (25-360° C.@10° C./min; 85 ml/min $N_2$ flow) of the sample after drying showed a weight loss of 4.0% between 40.3° C. and 144.2° C. $^1$H-NMR ($d_6$-DMSO) δ=0.83-0.91 (m, 2H), 1.11-1.20 (m, 2H), 2.48-2.62 (m, 1H, overlapping with DMSO peak), 3.17 (s, 2.3H), 4.01 (s, 2H), 4.17 (br s, 1H), 7.16 (d, 1H, J=8.0 Hz), 7.44 (d, 1H, J=7.7 Hz), 7.64 (d, 1H, J=7.7 Hz), 7.61-7.79 (m, 2H), 8.59 (d, 1H, J=8.4 Hz), 13.05 (br s, 1H) ppm.

Example 7: Preparation of Lesinurad Form APO-I

A mixture of Lesinurad sodium salt (2.5 g, 5.9 mmol) in HPLC grade methanol (15 mL) was sonicated briefly to achieve dissolution (5 minutes). To this solution was added hydrogen chloride (20 wt % in isopropanol, 1.07 g, 5.87 mmol) drop wise over 5 minutes. Immediate formation of a milky white precipitate was observed, and the mixture stirred for about 4.5 hours. The precipitated material was collected by filtration and dried under aspiration for 5 minutes, affording a colourless solid (0.82 g, 32% yield). The solid was further dried at room temperature in vacuo for 19 hours affording Lesinurad Form APO-I (0.76 g). PXRD analysis of the solid after drying was consistent with FIG. 1. $^1$H-NMR analysis of the dried solid indicated a weight percentage methanol of 6.8 wt %. The PXRD diffractogram of a capped sample of this material placed in stability chambers maintained at 27° C./60% RH showed no change after 17 days of storage.

Example 8: Preparation of Lesinurad Form APO-II

Lesinurad (200 mg, 0.495 mmol) was weighed into a vial and suspended in anhydrous ethanol (1 mL). The vial containing the suspension was placed inside a pre-heated reactor block set to 50° C., and further portions of ethanol (0.8 mL) were added to achieve dissolution. Hot filtration was performed and the solution was allowed to reach room temperature rapidly outside the reactor block. Upon stirring the resulting precipitate for 3 hours, the solid was collected by filtration to afford Lesinurad Form APO-II. The PXRD diffractogram of a sample prepared by this method is shown in FIG. 2.

Example 9: Preparation of Lesinurad Form APO-II

Lesinurad (200 mg, 0.495 mmol) was weighed into a vial and dissolved in anhydrous ethanol (3.8 mL) with brief sonication to facilitate dissolution. To this solution was added distilled water (2.5 mL) drop wise over 3 minutes. The clear solution was allowed to stir at room temperature for 2.5 hours, during which time a precipitate formed. The solid was collected by filtration and dried in vacuo for about 64 hours, affording Lesinurad Form APO-II (56.9 mg, 26% yield) having a PXRD consistent with FIG. 2 and a weight percentage ethanol of 8.3 wt % by $^1$H-NMR.

Example 10: Preparation of Lesinurad Form APO-II

A mixture of Lesinurad sodium salt (250 mg, 0.587 mmol) in anhydrous ethanol (2.75 mL) was sonicated briefly to achieve dissolution. Upon clarifying filtration, the solution was treated with a hydrogen chloride solution (20 wt % in isopropanol, 120 mg, 0.587 mmol) drop wise over 5 minutes and a fine white precipitate formed immediately. Stirring was continued for about 3 hours, whereupon the precipitate appeared as a very fine solid. The mixture was concentrated to approximately half volume using a steady nitrogen stream. After concentrating for 1 hour, the thick precipitate was collected by filtration, affording Lesinurad Form APO-II (101 mg, 38% yield). The PXRD diffractogram of a sample prepared by this method was consistent with FIG. 2.

Example 11: Preparation of Lesinurad Form APO-II

A mixture of Lesinurad sodium salt (2.25 g, 5.28 mmol) in anhydrous ethanol (25 mL) was sonicated briefly to afford a solution, to which was added a solution of hydrogen chloride (20 wt % in isopropanol, 22 g, 5.56 mmol) drop wise over 5 minutes. Immediate formation of a milky white precipitate was observed, and the mixture was stirred for 2 hours. The precipitated material was collected by filtration and dried under aspiration for 5 minutes, affording a colourless solid (1.25 g, 53% yield). The material was further dried at room temperature in vacuo for 3 hours. PXRD analysis after drying was consistent with FIG. 2. TGA analysis (25-360° C.@10° C./min; 85 ml/min N$_2$ flow) of the sample after drying showed a weight loss of 6.0% between 37.9° C. and 145.9° C. $^1$H-NMR (d$_6$-DMSO) δ=0.84-0.91 (m, 2H), 1.06 (t, 2.7H, J=7 Hz), 1.11-1.20 (m, 2H), 2.48-2.62 (m, 1H, overlapping with DMSO peak), 3.44 (q, 1.9H, J=7 Hz), 4.01 (s, 2H), 4.43 (br s, 1H), 7.16 (d, 1H, J=7.2 Hz), 7.44 (d, 1H, J=7.7 Hz), 7.64 (d, 1H, J=7.7 Hz), 7.60-7.79 (m, 2H), 8.59 (d, 1H, J=8.3 Hz), 13.06 (br s, 1H) ppm. The PXRD diffractogram of a capped sample of this material maintained at room temperature and ambient humidity showed no change after 28 days of storage.

Example 12: Preparation of Lesinurad Form APO-III

A suspension of Lesinurad (2.5 g, 6.2 mmol) and nicotinamide (0.83 g, 6.8 mmol) in anhydrous ethanol (52.5 mL) was heated to 75° C. to afford a solution. The solution was cooled to 60° C. over 20 minutes, at which time turbidity was observed. The mixture was cooled incrementally by decreasing the set temperature by 10° C. about every hour until reaching a temperature of 30° C., at which point the suspension was stirred for 0.5 hours and the heating discontinued. Upon stirring for a further 45 minutes, filtration afforded a solid which was dried in vacuo at about 35° C. for 3 hours (2.52 g, 77% yield). The PXRD diffractogram of a sample prepared by this method is shown in FIG. 3. $^1$H-NMR (d$_6$-DMSO) δ=0.82-0.92 (m, 2H), 1.10-1.20 (m, 2H), 2.48-2.62 (m, 1H, overlapping with DMSO peak), 4.01 (s, 2H), 7.17 (d, 1H, J=8.3 Hz), 7.40-7.55 (m, 2H), 7.57-7.80 (m, 4H), 8.12-8.26 (m, 2H), 8.59 (d, 1H, J=8.4 Hz), 8.71 (d, 1H, J=4.7 Hz), 9.05 (s, 1H), 13.01 (br s, 1H) ppm. $^{13}$C-NMR (d$_6$-DMSO) δ 7.3, 7.4, 13.0, 34.2, 121.8, 122.7, 123.4, 125.2, 126.6, 126.9, 127.3, 128.2, 128.7, 129.7, 131.4, 133.5, 135.2, 143.2, 148.7, 151.9, 153.6, 166.5, 169.1 ppm. The PXRD diffractogram of capped and uncapped samples of this material placed in stability chambers maintained at both 27° C./60% RH and 40° C./75% RH showed no change after 18 days of storage.

Example 13: Preparation of Lesinurad Form APO-III

A suspension of Lesinurad (250 mg, 0.62 mmol) and nicotinamide (83 mg, 0.68 mmol) in anhydrous ethanol (6.4 mL) was heated to 75° C. to dissolve. Upon hot filtration, the filtrate was returned to the heat and the set temperature decreased to 60° C. After 0.5 hour, the solution was seeded with a small quantity of Lesinurad Form APO-III, and the temperature decreased incrementally by 5° C. about every 15 minutes until reaching 30° C. After holding at 30° C. for 15 minutes, the heating was turned off and the mixture stirred a further 10 minutes before the product was isolated by filtration, affording Lesinurad Form APO-III (203.7 mg, 63% yield). PXRD of the sample was consistent with FIG. 3.

Example 14: Preparation of Lesinurad Form APO-III

A suspension of Lesinurad (500 mg, 1.24 mmol) and nicotinamide (166 mg, 1.36 mmol) in anhydrous ethanol (10.5 mL) was dissolved by heating in a 75° C. oil bath. Upon dissolution, the set temperature was decreased to 60° C. and held for about 1 hour. The set temperature was then decreased to 50° C. and the temperature was subsequently decreased incrementally by 10° C. over the course of 2 hours, at which time a temperature of 30° C. was reached. The heating was turned off, and after stirring 1 additional hour, filtration afforded Lesinurad Form APO-III (590 mg, 90%). The solid was further dried in vacuo at 40° C. for about 6 hours. PXRD of the sample was consistent with FIG. 3.

Example 15: Preparation of Single Crystals of Lesinurad Form APO-III

A small amount (approximately 100 mg) of Lesinurad Form APO-III was dissolved in DMSO (0.2 mL). The solution was frozen in a refrigerator (~2-8° C.) and acetone (1 mL) was slowly added to create two layers. The resulting biphasic solution was left undisturbed at room temperature for approximately 2 months. Crystals were collected after gently decanting off the solvent, with one crystal being selected for SCXRD analysis. FIG. 4 depicts an ORTEP illustration of the molecular structure of the Form APO-III crystals prepared by this method.

Example 16: Stability Study of Lesinurad Form APO-III

The stability of Lesinurad Form APO-III was assessed under various stress conditions as outlined in Table 5. As shown in Table 5, Lesinurad Form APO-III demonstrated good stability to dry heat, heat/humidity and light exposure, with no significant loss of Lesinurad, and only minor increases in the unidentified impurity levels (total degradation less than 0.10%). Unlike the Lesinurad proline co-crystal tested in Reference Example B, Lesinurad Form APO-III did not exhibit signs of hygroscopicity.

TABLE 5

Results of stability studies of Lesinurad Form APO-III

| Stress Condition | Total Identified Impurity (area %) | Major Unidentified Impurity (area %) (RRT) | Total Unidentified Impurity (area %) | Total Impurities (area %) |
|---|---|---|---|---|
| Non-stressed sample | 0.09 | 0.08 (0.91) | 0.24 | 0.33 |
| Sample (open) subjected to dry heat (Solid State, 60° C./ ambient RH), 21 Days) | 0.10 | 0.09 (0.91) | 0.30 | 0.40 |
| Sample (open) subjected to heat/humidity (Solid State, 40° C./75% RH, 21 Days) | 0.09 | 0.09 (0.91) | 0.29 | 0.38 |
| Sample wrapped in foil subjected to light exposure (control) (200 W · hr/ m² UV Light + 1.2M LUX hr Fluorescent Light) | 0.10 | 0.09 (0.92) | 0.32 | 0.42 |
| Sample subjected to light exposure (200 W · hr/ m² UV Light + 1.2M LUX hr Fluorescent Light) | 0.10 | 0.09 (0.92) | 0.35 | 0.46 |

Reference Example A: Lesinurad Sodium Salt

A 0.2 M ethanolic solution of Lesinurad (2.50 g, 6.18 mmol) was cooled to between 0° C. to 5° C. in an ice bath, and treated with a 1 M solution of sodium hydroxide (247 mg, 6.18 mmol) that was added drop wise from an addition funnel. The mixture was stirred for 0.5 h, clarified by filtration and concentrated. Co-distillation with dichloromethane was performed 3 times and the product further dried in vacuo at 35° C. for 3.5 hours, affording Lesinurad sodium salt (2.54 g, 97% yield). Lesinurad sodium salt prepared in this manner was used for the experiments described herein.

Reference Example B: Preparation of the Lesinurad:Proline Co-Crystal of WO 2015/095703 A1

The title solid form of Lesinurad was prepared according to the procedure in Example 14 of WO 2015/095703 A1. A suspension of Lesinurad (1 g) in ethyl acetate (63 mL) was sonicated at room temperature for 30 minutes in order to achieve dissolution. Proline (570 mg) was added to the solution, and the resulting suspension was stirred at room temperature for 26 hours, at which time the suspension was isolated by filtration to afford a solid (872.9 mg, 68% yield) having a PXRD diffractogram consistent with FIG. 22 in WO 2015/095703 A1. The solid, in an open container, was placed in a stability chamber maintained at 40° C./75% RH for 7 days. Following storage, the Lesinurad proline co-crystal had shown itself to be hygroscopic, with a mass increase of 38 wt %.

What is claimed is:

1. A crystalline form of Lesinurad characterized by a powder X-ray diffraction (PXRD) diffractogram comprising peaks, expressed in degrees 2θ (±0.2°), at 7.8°, 15.1°, and 27.0°.

2. The crystalline form of Lesinurad of claim 1, characterized by a PXRD diffractogram further comprising at least three peaks, expressed in degrees 2θ (±0.2°), selected from the group consisting of: 14.5°, 15.6°, 16.4°, 17.6°, 18.5°, 19.9°, 22.1°, 23.5°, 25.9°, and 29.3°.

3. The crystalline form of Lesinurad of claim 1, characterized by a PXRD diffractogram further comprising peaks, expressed in degrees 2θ (±0.2°), at 14.5°, 15.6°, 16.4°, 17.6°, 18.5°, 19.9°, 22.1°, 23.5°, 25.9°, and 29.3°.

4. The crystalline form of Lesinurad of claim 2, having a weight percentage of methanol of at least approximately 3.0 wt %.

5. The crystalline form of Lesinurad of claim 2, having a molar ratio of Lesinurad to methanol of approximately 1:0.5.

6. A crystalline form of Lesinurad characterized by a powder X-ray diffraction (PXRD) diffractogram comprising peaks, expressed in degrees 2θ (±0.2°), at 7.9°, 15.2°, 16.5°, and 25.4°.

7. The crystalline form of Lesinurad of claim 6, characterized by a PXRD diffractogram further comprising at least two peaks, expressed in degrees 2θ (±0.2°), selected from the group consisting of: 14.4°, 15.7°, 17.7°, 18.4°, 22.1°, 22.8°, 23.5°, 26.5°, 28.8°, and 29.3°.

8. The crystalline form of Lesinurad of claim 6, characterized by a PXRD diffractogram further comprising peaks, expressed in degrees 2θ (±0.2°), at 14.4°, 15.7°, 17.7°, 18.4°, 22.0°, 22.8°, 23.5°, 26.5°, 28.8°, and 29.3°.

9. The crystalline form of Lesinurad of claim 7, having a weight percentage of ethanol of at least approximately 4.3 wt %.

10. The crystalline form of Lesinurad of claim 7, having a molar ratio of Lesinurad to ethanol of approximately 1:0.5.

11. A co-crystal of Lesinurad with nicotinamide.

12. The co-crystal of claim 11, wherein the molar ratio of Lesinurad to nicotinamide is approximately 1:1.

13. The co-crystal of claim 12, wherein the co-crystal is characterized by a powder X-ray diffraction (PXRD) diffractogram comprising peaks, expressed in degrees 2θ (±0.2°), at 6.2°, and 19.9°.

14. The co-crystal of claim 13, characterized by a PXRD diffractogram further comprising at least four peaks, expressed in degrees 2θ (±0.2°), selected from the group consisting of: 7.6°, 10.3°, 14.1°, 15.3°, 17.8°, 21.1°, 23.4°, 25.7°, and 27.2°.

15. The co-crystal of claim 13, characterized by a PXRD diffractogram further comprising peaks, expressed in degrees 2θ (±0.2°), at 7.6°, 10.3°, 14.1°, 15.3°, 17.8°, 21.1°, 23.4°, 25.7°, and 27.2°.

* * * * *